United States Patent [19]

Ohe

[11] Patent Number: 4,729,379

[45] Date of Patent: Mar. 8, 1988

[54] DIGITAL SUBTRACTION-IMAGING APPARATUS UTILIZING CARDIAC-SYNCHRONIZED SUBTRACTION METHOD

[75] Inventor: Mitsuo Ohe, Ootawara, Japan

[73] Assignee: Kabushiki Kaisha Toshiba, Kawasaki, Japan

[21] Appl. No.: 945,542

[22] Filed: Dec. 23, 1986

[30] Foreign Application Priority Data

Dec. 27, 1985 [JP] Japan ................... 60-294648

[51] Int. Cl.⁴ .................................................. A61B 6/00
[52] U.S. Cl. ...................................... 128/654; 128/659; 128/708; 358/111; 378/95; 378/99
[58] Field of Search ............... 128/654, 659, 696, 708; 358/111; 364/414; 378/99, 95

[56] References Cited

U.S. PATENT DOCUMENTS

| | | | |
|---|---|---|---|
| 4,204,225 | 5/1980 | Mistretta | 128/695 X |
| 4,433,428 | 2/1984 | Haendle et al. | 378/99 X |
| 4,611,340 | 9/1986 | Okazaki | 128/708 X |

FOREIGN PATENT DOCUMENTS 0050900 3/1985 Japan .................... 128/654

OTHER PUBLICATIONS

Hirji et al., "EKG-Gated Digital Subtraction Angiography in the Detection of Pulmonary Emboli," Radiology, vol. 152, No. 1, pp. 19-20, Jul. 1984.

*Primary Examiner*—William E. Kamm
*Assistant Examiner*—Ruth S. Smith
*Attorney, Agent, or Firm*—Finnegan, Henderson, Farabow, Garrett & Dunner

[57] ABSTRACT

In a digital subtraction imaging apparatus, the digital subtraction between mask images and contrast images is carried out in synchronism with cardiac beats of an object under medical examination such as a patient. The subtraction-imaging apparatus includes a first memory, a second memory, a cardiac-synchronized subtraction unit, and a central processing unit. When the number of the contrast images acquired within one cardiac cycle is smaller than that of the mask images, for example, when four contrast images and five mask images are obtained, the digital subtraction by the subtraction unit, under the control of the central processing unit, is performed between four contrast images and only four mask images, without using the fifth mask image. Conversely, when the number of the contrast images is greater than that of the mask images, for example, when five contrast images and four mask images are obtained, the digital subtraction is effected between four mask images and four contrast images, and furthermore, is performed between the fourth mask image and the fifth contrast image, under the control of the central processing unit.

13 Claims, 7 Drawing Figures

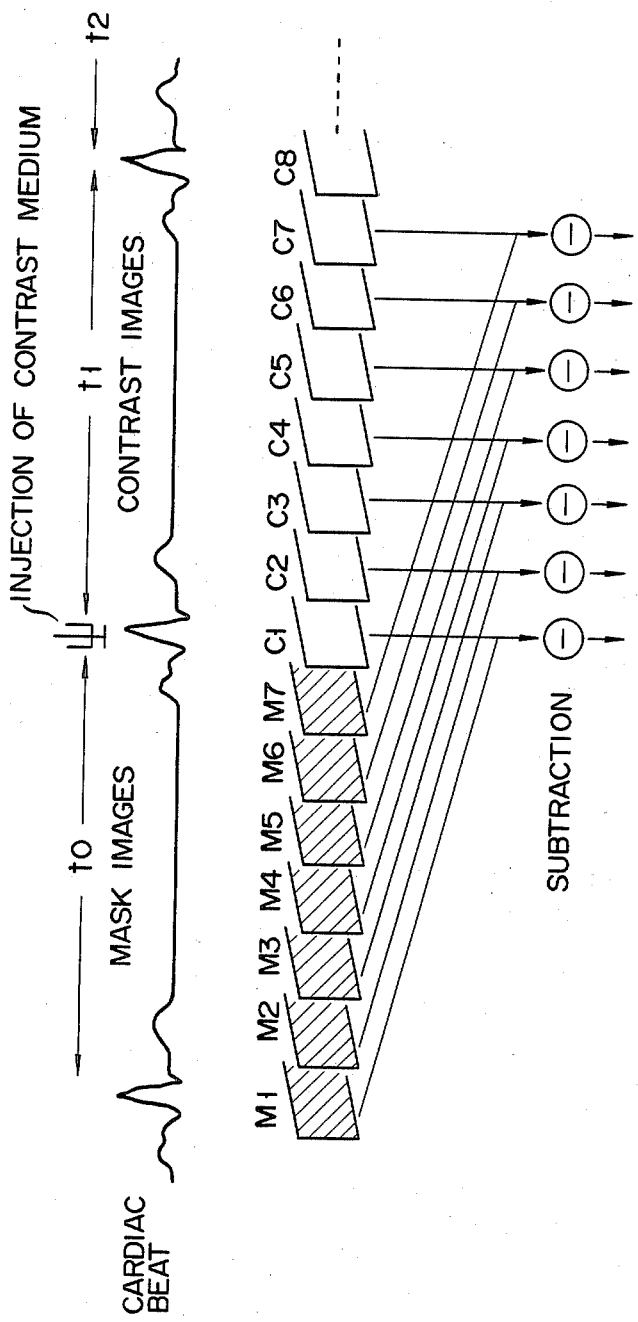

DIGITAL SUBTRACTION-IMAGING APPARATUS UTILIZING CARDIAC-SYNCHRONIZED SUBTRACTION METHOD

BACKGROUND OF THE INVENTION

1. Field of the Invention

The present invention relates to a digital fluoroscopic apparatus, and more particularly to a digital subtraction-imaging apparatus wherein digital subtraction between mask images and contrast images is performed in synchronism with heartbeats.

2. Description of Related Art

In a known digital fluoroscopic apparatus, in order to acquire a plurality of X-ray images and perform image processing, bone or muscle image components are erased from an image, by subtraction between an image (mask image) taken before an X-ray contrast medium is injected into a object under medical examination such as a patient, and an image (contrast image) taken after the injection of an X-ray contrast medium, and only an image component reflecting the X-ray contrast medium can be obtained as an image.

A cardiac-synchronized subtraction method is available for use in a digital fluoroscopic apparatus of this type. According to this method, in order to examine a patient's heart, mask images corresponding to one cardiac cycle are acquired, and subtraction is performed between these mask images and contrast images of the same cardiac beat phase, thereby removing image components due to the cardiac beat from the subtraction image.

This known method will now be described with reference to FIGS. 1, 2A, and 2B.

First, mask images are acquired for one cardiac period ("$t_0$" in FIG. 1), at a rate of 30 frames/sec, i.e., for about 30 frames at a rate of 60 heartbeats/min, as shown in FIG. 1. In FIG. 1, mask images are acquired only at 7 frames/sec, for the purpose of simplicity. An X-ray contrast medium is injected into the object under medical examination, and a predetermined number of contrast images are acquired at respective cardiac periods $t_1, t_2, t_3, \ldots, t_n$. Then, subtraction is performed successively between mask images M1 to M7 and contrast images C1 to Cn of the same cardiac beat phase, as shown in FIG. 2A. Subsequently, as shown in FIG. 2B, subtraction is performed successively between mask images M1 to M7 and contrast images C8 to C14 of a second heartbeat, as shown in FIG. 2B. In this manner, the same mask images M1 to M7 are selectively used, and subtraction is performed successively between these mask images M1 to M7 and corresponding contrast images C1 to Cn. The cardiac beat phases of the mask and contrast images are allowed to coincide, i.e., are subjected to contrast synchronization by use of an electrocardiogram.

This conventional cardiac-synchronized subtraction method is known from, for example, "EKG-Gated Digital Subtraction Angiography in the Detection of Pulmonary Emboli[1]" by Mohamed Hirji et al. published in 1984 "Radiology", 152; Pages 19–22.

In such a cardiac subtraction process, when the heart rate remains constant during image acquisition, no problems occur, since the number of mask images always coincides with that of contrast images acquired during each cardiac period. However, the heart rate can change. In particular, when an X-ray contrast medium is injected, the cardiac beat rate can be temporarily disturbed. More specifically, variations in heartrate (i.e., the number of heartbeats) cause variations in respective cardiac periods $t_1$ to $t_n$. As a result, the number of the contrast images acquired during each cardiac period may increase or decrease. In this situation, desired subtraction between mask and contrast images of the same cardiac beat phase cannot be performed. In other words, when subtraction is performed between mask and contrast images of different cardiac beat phases (i.e., when non cardiac-synchronized subtraction is performed), an artifact might appear in the obtained subtraction images.

The present invention has been in view of the above situation, and has as its object to provide a cardiacsynchronized subtraction system which can perform subtraction, without interruption, by reliably allowing cardiac beat phases to coincide even when the cardiac beat rhythm is disturbed or the number of heart beats varies.

SUMMARY OF THE INVENTION

To achieve the foregoing object and the features of the invention, a digital subtraction imaging apparatus comprises first memory means for temporarily storing a plurality of images, as mask images, which have been acquired during at least one cardiac cycle before an X-ray contrast medium is penetrated into a region of interest (ROI) of an object under medical examination, second memory means for temporarily storing a plurality of images, as contrast images, which have been acquired during a plurality of cardiac cycles, succeeding said one cardiac cycle, after the X-ray contrast medium has penetrated into the ROI of the object, means for performing digital subtraction in synchronism with cardiac beats of said object, between said successive mask images, read out from the first memory means, and said corresponding contrast images, read out from the second memory means, and, means for controlling said digital subtraction means in such a manner that when the number of contrast images acquired within an arbitrary one cardiac cycle is smaller than that of the mask images stored in the first memory means and acquired within said one cardiac cycle, said subtraction means performs digital subtraction between all of said contrast images and the corresponding mask images, withholding a predetermined number of said mask images which do not correspond to said contrast images, with respect to the cardiac beats, whereas, when the number of contrast images acquired within said arbitrary one cardiac cycle is greater than that of the mask images acquired within said one cardiac cycle, said digital subtraction is carried out by utilizing all of said contrast images and by repeatedly utilizing at least one of said mask images, in addition to all of the corresponding mask images, with respect to the cardiac beats.

BRIEF DESCRIPTION OF THE DRAWINGS

For a better understanding of the invention, the following description will be read in conjunction with the drawings, in which:

FIGS. 1, 2A, and 2B illustrate operations of a known digital subtraction method for mask and contrast images;

DESCRIPTION OF THE PREFERRED EMBODIMENT

GENERAL DESCRIPTION OF THE DIGITAL SUBTRACTION METHOD

In a known circuit configuration, pulsatory X-rays are generated, the surface of an object under medical examination such as a patient is irradiated with the pulsatory X-rays using X-ray unit 90 in association with X-ray contrast medium injection 70 to obtain X-ray images, the obtained X-ray images are temporarily stored in memory devices, and thereafter, digital subtraction is performed between mask images and contrast images. Such a known digital subtraction imaging method is disclosed in, e.g., U.S. Pat. No. 4,204,226 to Mistretta, issued on May 20, 1980, which is incorporated by reference herein as background material. Since the digital subtraction imaging apparatus of the present invention employs such a known circuit configuration, a detailed description thereof is omitted herein. Only circuit operations and configuration details unique to the present invention will be described below in detail.

BASIC IDEA OF CARDIAC-SYNCHRONIZED SUBTRACTION METHOD

Before describing various types of preferred embodiments according to the invention the, basic idea of cardiac-synchronized subtraction will now be summarized.

The cardiac-synchronism subtraction system is characterized in that it comprises first and second memory means, subtraction-processing means, and control means. The first memory means stores a plurality of mask images acquired within one cardiac cycle, or heartbeat period. The second memory means stores a plurality of contrast images acquired within a plurality of cardiac cycles when a contrast medium is injected into a region of interest (ROI) after the mask images have been acquired. The subtraction-processing means sequentially reads out corresponding mask and contrast images from the first and second memory means, respectively, and performs subtraction therebetween. When the number of contrast images of one cardiac cycle to be subjected to subtraction is smaller than the number of mask images of one cardiac cycle stored in the first memory means, the control menas does not read out the remaining mask images. In other words, these mask images are not read out from the first memory means to perform such subtraction. Thus, the subtraction is completed. Conversely, when the number of the contrast images of one cardiac cycle exceeds the number of mask images, the control means reads out the mask images repeatedly, and subjects the readout mask images to subtraction in accordance with a predetermined rule.

ARRANGEMENT OF CARDIAC-SYNCHRONIZED SUBTRACTION SYSTEM

Figure 3:
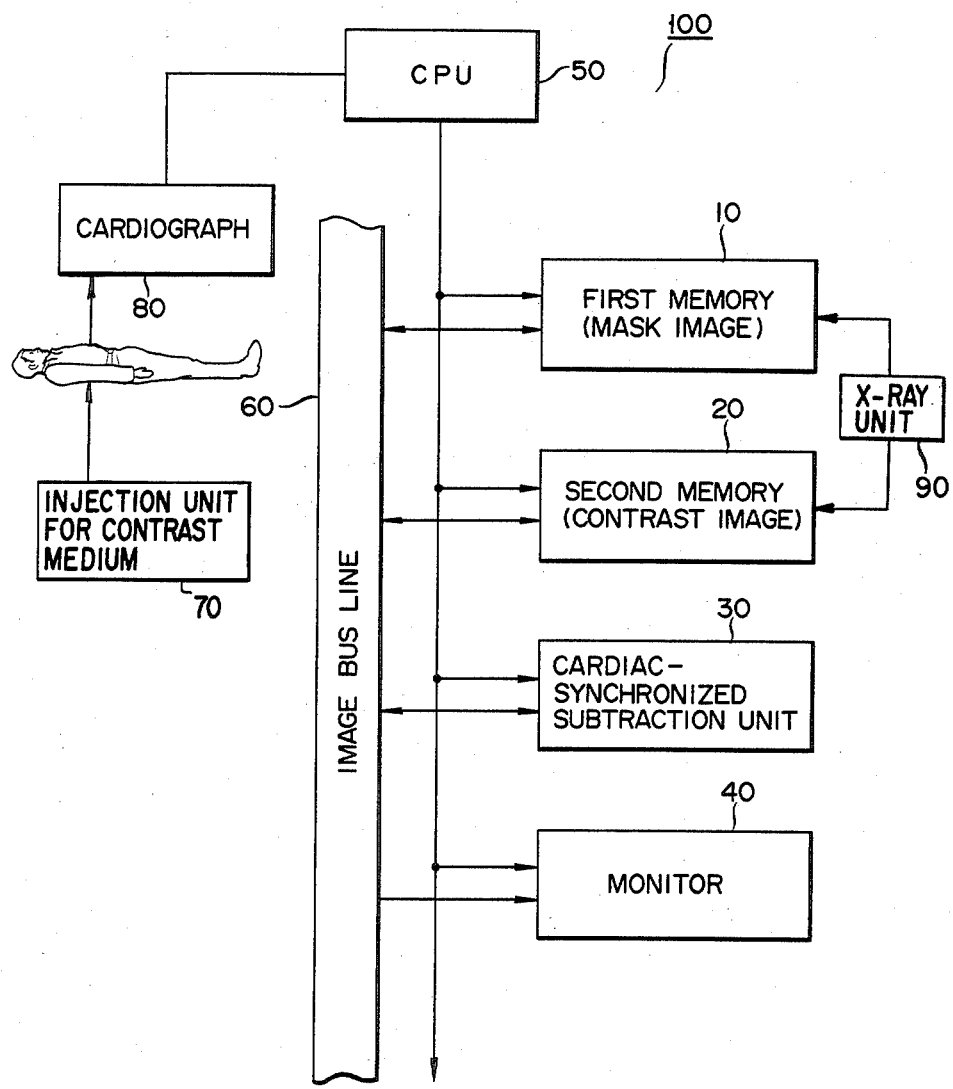
FIG. 3 is a schematic block diagram of a major circuit of a digital subtraction-imaging apparatus 100 according to one embodiment.

FIG. 3 is a block diagram showing a major unit of subtraction-imaging system 100 of an apparatus according to a first embodiment of the present invention.

Figure 1:
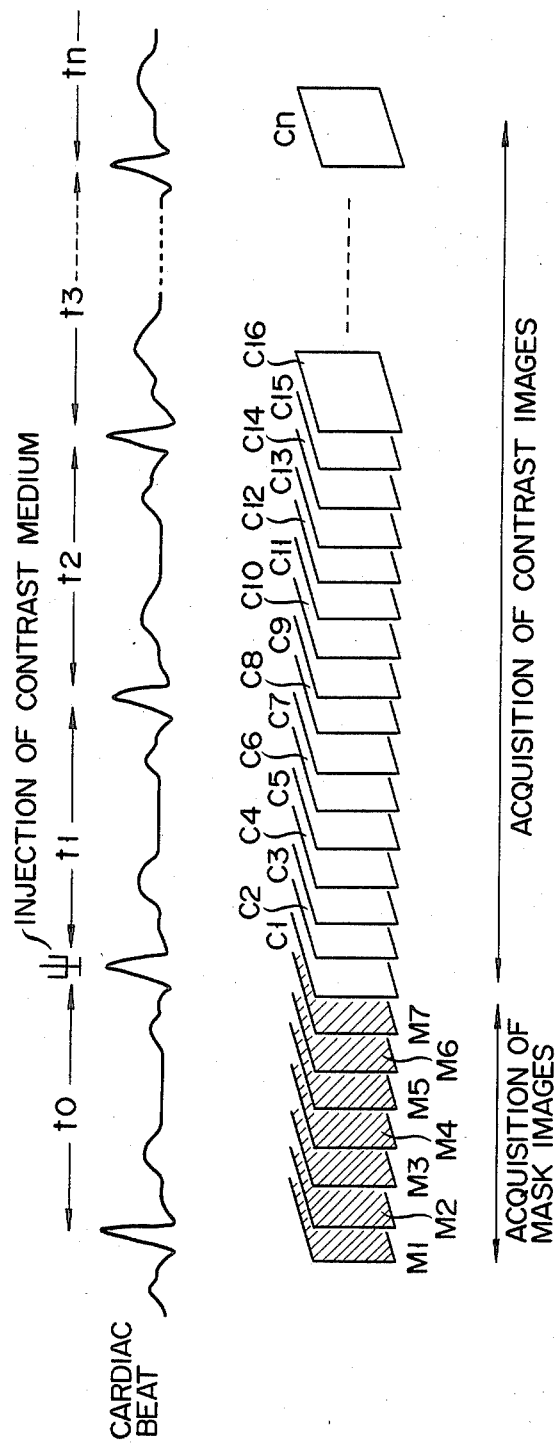
Figure 2B:
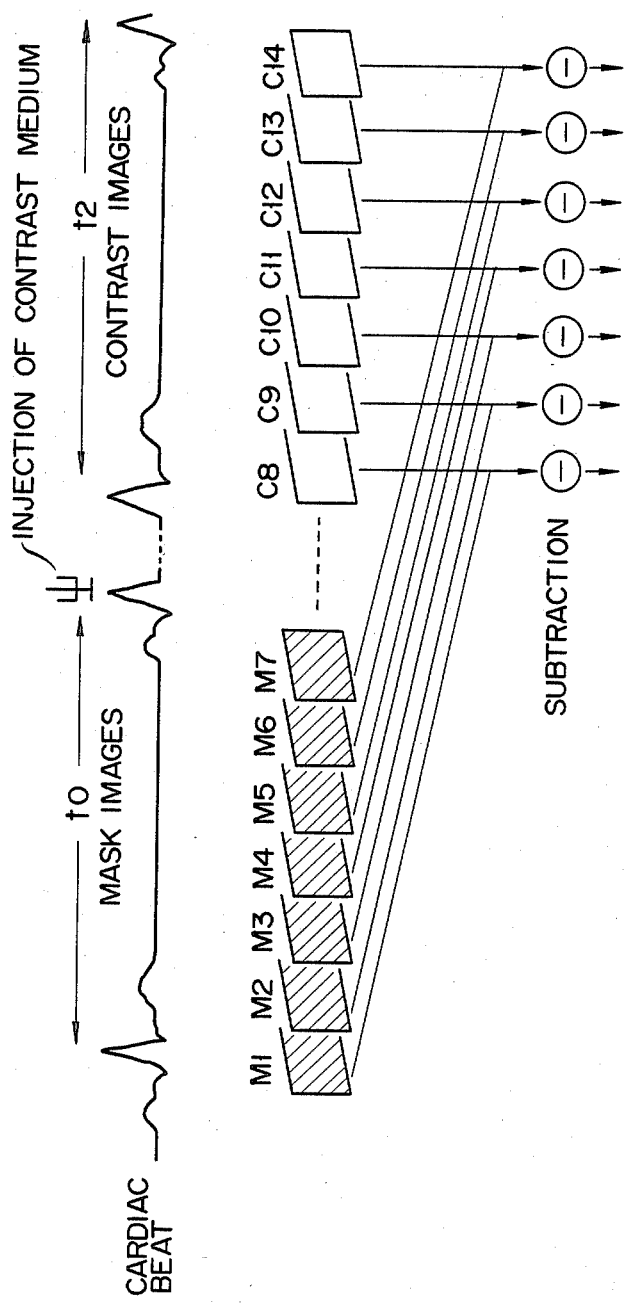

First memory 10 is provided for storing a plurality of mask images acquired within one cardiac cycle of a object under medical examination, i.e., a patient (not shown). For example, memory 10 stores mask images M1 to M7 shown in FIGS. 1, 2A, and 2B.

Second memory 20 is provided for storing a plurality of contrast images acquired within cardiac periods, e.g., t1 and t2, after the mask images have been acquired. For example, memory 20 stores contrast images C1 to Cn shown in FIGS. 1, 2A, and 2B.

Figure 6:
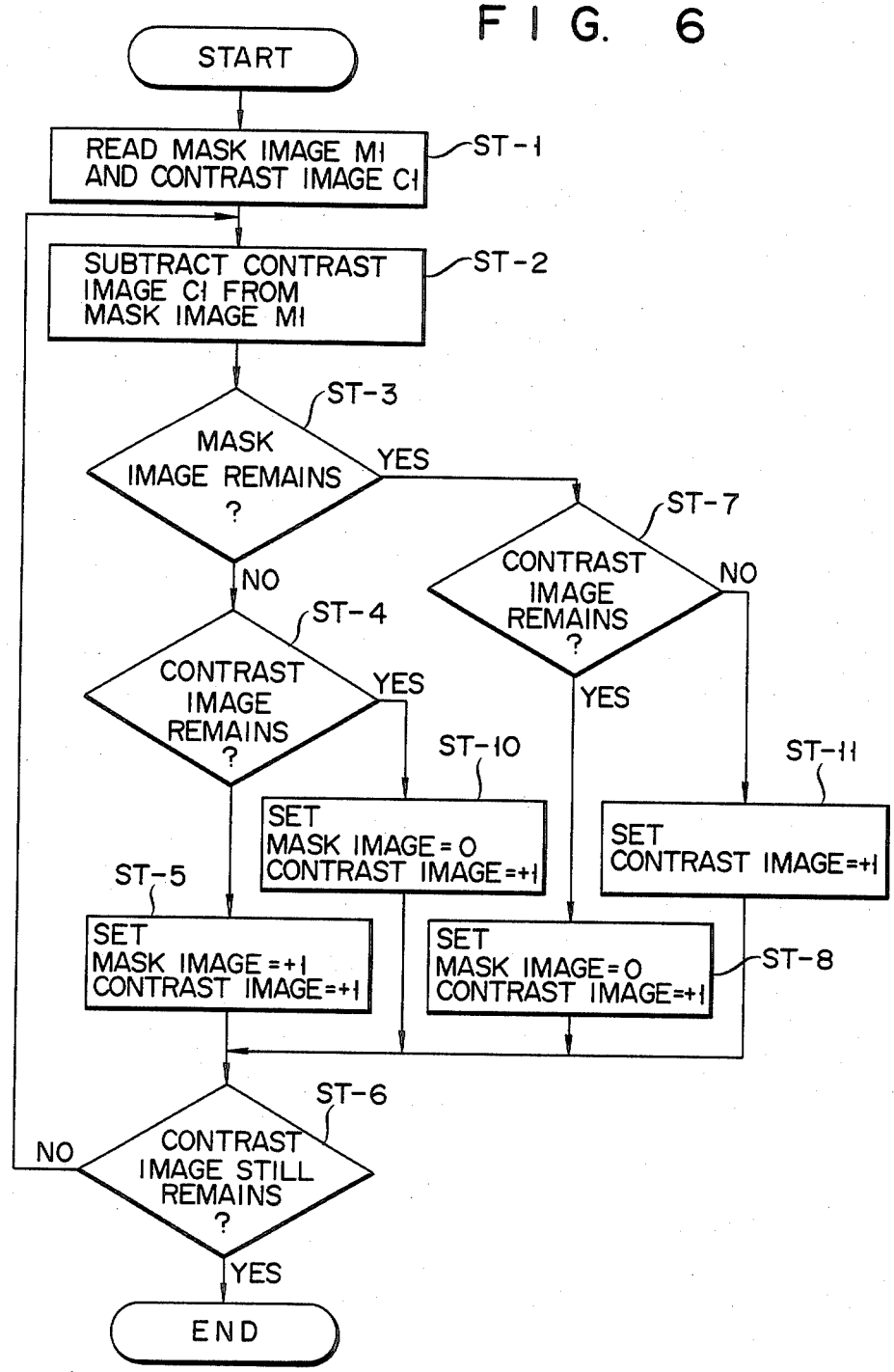
FIG. 6 is a flow chart for explaining the overall operations of the cardiac-synchronized subtraction methods.

Cardiac-synchronized subtraction unit 30 is provided to successively read out corresponding mask and contrast images from first and second memories 10 and 20, respectively, and perform subtraction therebetween. Usually, for example, mask and contrast images M1 and C1 are first read out from memories 10 and 20, respectively. First mask image M1 is subtracted from first contrast image C1, and an image having only an image component reflecting the X-ray contrast medium at that point (i.e., the point in time when image C1 was acquired) is obtained in accordance with a predetermined rule. This rule is described hereafter in connection with FIG. 6. Subsequently, mask and contrast images M2 and C2 are read out from memories 10 and 20, respectively, and subtraction therebetween is performed. An image having only an image component corresponding to the X-ray contrast medium, when image C2 was acquired, is obtained. In this manner, mask and contrast images are sequentially read out and are subjected to subtraction. When all the mask images (7 mask images M1 to M7 in the case shown in the drawing) stored in memory 10 are used, they are repeatedly, selectively used to correspond to the following contrast images C8 to C14 (see FIG. 2B). A case wherein the number of mask images and the number of contrast images during one cardiac cycle do not coincide with each other, due to a variation in the number of heartbeats, will be described later.

Monitor 40 is provided to display an image containing only an image component reflecting the X-ray contrast medium, obtained by processing unit 30.

CPU (Central Processing Unit) 50 is connected to control the operations of first and second memories 10 and 20, processing unit 30, and monitor 40. When the number of contrast images corresponding to one cardiac cycle stored in second memory 20 is smaller than that of mask images stored in first memory 10, CPU 50 does not read out the remaining mask images and thus does not use them in the subtraction process. When the number of contrast images corresponding to one cardiac cycle is larger than the number of mask images, CPU 50 reads out the same mask images again in sequence, and uses them in the subtraction process. In other words, CPU 50 acquires images and an electrocardiogram simultaneously, using cardiograph 80, and matches the cardiac beat phases of the mask and contrast images with reference to the R-wave (see FIGS. 4 and 5) if the electrocardiogram.

Figure 4:
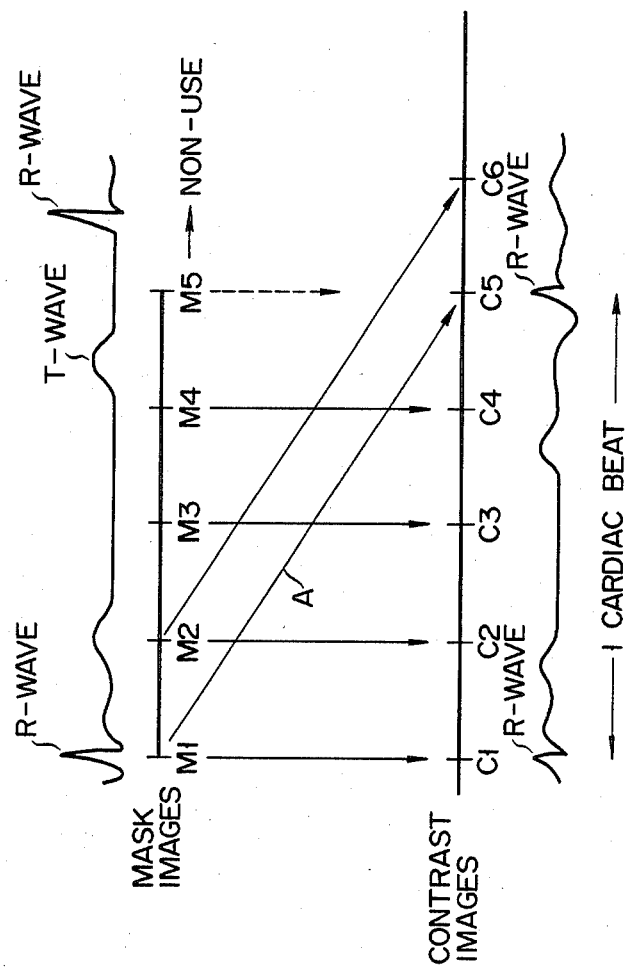
FIGS. 4 and 5 illustrate cardiac-synchronized subtraction methods performed in the system shown in FIG. 3.
Figure 5:
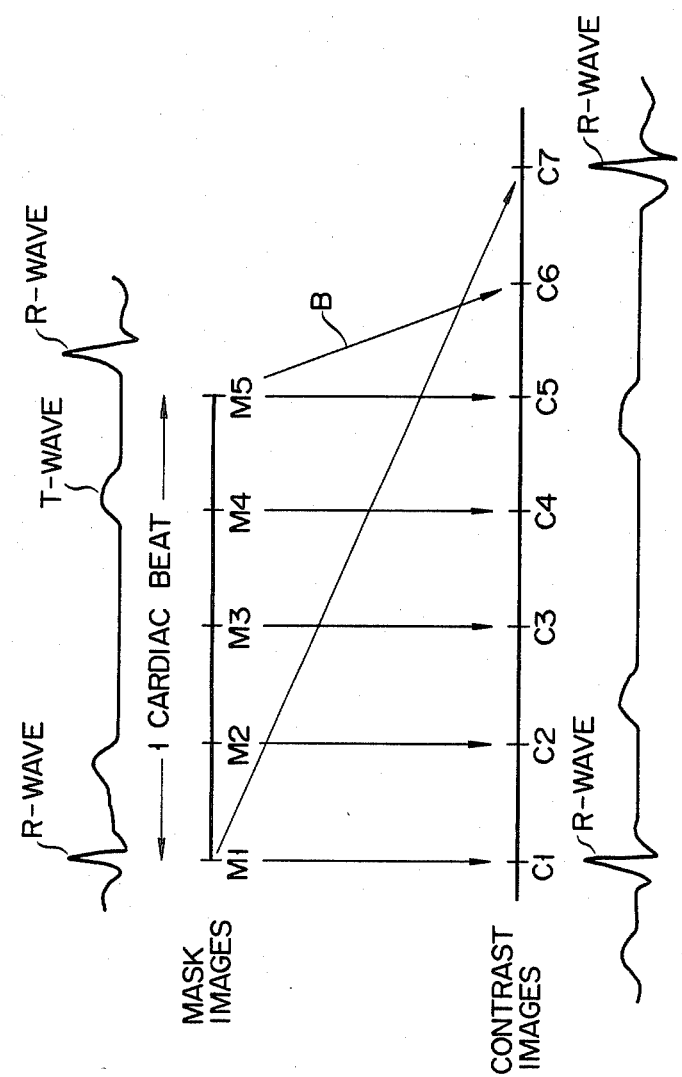

According to the present invention, when the number of heartbeats differs between the mask and contrast images, CPU 50 performs control as shown in FIGS. 4 and 5, as will be described later.

As is apparent from FIG. 3, first and second memories 10 and 20, respectively, cardiac-synchronized subtraction unit 30, and monitor 40 achieve communication of image data through image bus line 60.

WHEN CONTRAST IMAGE ACQUISITION TIME IS LONGER THAN MASK IMAGE ACQUISITION TIME

In general, when X-ray images are acquired using a digital subtraction-imaging apparatus of this type, they are acquired while the patient has temporarily stopped his respirating. More specifically, mask and contrast images are acquired within a short period of about 10 to 20 sec, at an image acquisition speed of, e.g., 30 frames/-sec.

In this case, disturbance of heartbeat rate often occurs during the cardiac cycle. In particular, it is clinically known that when an X-ray contrast medium is injected into a patient, a variation occurs in the cardiac period, i.e., the number of heartbeats.

FIG. 4 shows processing performed by CPU 50 when the number of the heartbeats, upon contrast image acquisition, is larger than that upon mask image acquisition, i.e., when one cardiac period becomes short. For the purpose of simple description, in FIG. 4, only four contrast images C1, C2, C3, and C4 can be acquired while five mask images M1, M2, M3, M4, and M5 are acquired. The contrast images are shown under the mask images, to clarify their correspondence.

In this case, the sequentially following R-wave (corresponding to C5) appears before all mask images M1, M2, M3, M4, and M5 acquired during one cardiac period are used. Thus, image M5 is not used and cardiac synchronization is performed using the next R-wave. In other words, images M1 and C5 are allowed to coincide.

WHEN CONTRAST IMAGE ACQUISITION TIME IS SHORTER THAN MASK IMAGE ACQUISITION TIME

FIG. 5 shows processing performed by CPU 50 when, in contrast to the case of FIG. 4, the number of the heart beats, upon contrast image acquisition, is smaller than that upon mask image acquisition, i.e., when one cardiac period becomes long and, e.g., six contrast images C1, C2, C3, C4, C5, and C6 are acquired.

In this case, the next sequential R-wave (corresponding to C7) does not appear, even after all mask images M1, M2, M3, M4, and M5 have been used. Thus, for the sixth contrast image C6, the fifth mask image M5, the same as previously used for 5th contrast image C5, is used. Regarding a case wherein one cardiac period becomes still longer and, e.g., seven contrast images are acquired, the fifth image M5 is used also for the seventh image according to a predetermined rule. This rule is described hereafter in connection with FIG. 6.

When cardiac-synchronized subtraction is performed in this manner, under the control of CPU 50, the cardiac phases are synchronized whenever an R-wave appears. Even if the cardiac beat rate is temporarily disturbed, mask and contrast images having the same phases can be obtained at the following R-wave.

OVERALL OPERATION

Cardiac-synchronized subtraction performed by CPU 50, in the above manner, will be now described with reference to the flow chart of FIG. 6 and FIGS. 3, 4, and 5.

First, the first mask and contrast images M1 and C1, respectively, are read out (step ST-1), subtraction therebetween is performed by cardiac-synchronized unit 30, and the subtraction result is displayed on monitor 40 (step ST-2). Subsequently, a check is performed to determine whether all mask images M1 to M5 have been read out (step ST-3). If NO in step ST-3, a check is then performed to determine whether all of contrast images, e.g., C1 to C6, of one cardiac cycle have been read out (step ST-4). If NO in step ST-4, the numbers of mask and contrast images which have been read out are incremented by one, respectively (step ST-5). In addition, a check is performed to determine whether all the contrast images of all the cardiac cycles have been read out (step ST-6). If NO in step ST-6, a succeeding mask image (e.g., image M2 whose number is obtained by incrementing in step ST-5), and a succeeding contrast image (e.g., image C2 whose number is obtained by incrementing in step ST-5) are read out, and processing following subtraction is repeated. When all the mask images are read out, YES is obtained in step ST-3, and a check is carried out to determine whether all the contrast images of one cardiac cycle have been read out (step ST-7). Usually, since the numbers of mask and contrast images are the same, YES is obtained in step ST-7. In this case, the number of mask images is returned to 0 and the number of the contrast images is incremented by one, in step ST-8, and the flow advances to the processing of the next cardiac cycle. The above operation is then repeated. When subtraction for all the cardiac cycles has been completed, YES is obtained in step ST-6, and the processing ends. In the above description, a normal case is described. In other words, the number of mask images and that of contrast images for one cardiac cycle are the same.

A case will now be described wherein the number of contrast images is smaller than that of mask images for one cardiac period (see FIG. 4). In this case, readout of all the contrast images (C1 to C4) for one cardiac cycle ends before the readout of all the mask images (M1 to M5) ends. Therefore, YES is obtained in step ST-4. The number of mask images is returned to 0, in step ST-10, and the number of contrast images is incremented by one. As a result, after mask and contrast images M1 to M4 and C1 to C4, respectively, are used (in the above-described case of FIG. 4), the number of mask images is returned to 0. Thus, mask image M5 is left unused, the number of contrast images is incremented by 1, and images M1 and C5 are allowed to coincide, as is indicated by arrow A in FIG. 4. Thereafter, discrimination step ST-6 is performed in the same manner as in the usual (i.e., normal) case described above, and the processing following subtraction is repeated.

A case will now be described wherein the number of contrast images is larger than that of mask images for one cardiac period. In this case, readout of all the mask images ends before the readout of all the contrast images of one cardiac cycle ends. Therefore, YES is obtained in step ST-3, and discrimination step ST-7 is then performed. In the normal case, YES, is obtained in step ST-7, as in the above case. However, since the number of contrast images is larger than that of mask images, NO is obtained in step ST-7. In this case, the number of mask images is left unchanged, and only the number of contrast images is incremented by one (step ST-11). As a result, mask and contrast images M1 to M5 and C1 to C5, respectively, are used (in the above-described case of FIG. 5), and thereafter, mask image M5 is used with contrast image C6, as is indicated by arrow B in FIG. 5. This operation is repeated until YES is obtained in step ST-7. Thereafter, discrimination step ST-6 is performed, in the same manner as in the usual (i.e., normal) case described above, and the processing following subtraction process of step ST-2 is repeated.

As has been described above in detail, according to the present invention, when the number of contrast images is smaller than that of mask images for specific one cardiac period, the remaining mask images are left unused in the subtraction process. When the number of contrast images exceeds that of mask images, the previously used mask images are used again according to the predetermined rule, described above in connection with FIG. 6. Therefore, even when the heartbeat rate is disturbed or varies during contrast image acquisition, subtraction can be performed by reliably synchronizing the cardiac beat phases of the mask and contrast images so as to avoid defects in the image quality.

MODIFICATIONS

An embodiment of the present invention has been described above. However, the present invention is not limited to this. Various changes and modifications may be made within the spirit and scope of the present invention.

For example, in the above embodiment, both mask and contrast images are synchronized with respect to the R-wave. In place of such synchronization, mask and contrast images can be synchronized at instants of R- and T-waves. This is because synchrnoization is preferably performed at an instant when the heart beats.

In the embodiment shown in FIG. 5, it is possible to perform subtraction between fourth mask image M4 and fifth contrast image C5, and between fifth image M5 and sixth contrast image C6.

What is claimed is:

1. A digital subtraction-imaging apparatus comprising:
    means for providing X-ray images through an object exposed to an X-ray source;
    means for injecting said object with an X-ray contrast medium;
    first memory means for temporarily storing a plurality of images, as mask images, which have been acquired during at least one cardiac cycle before said X-ray contrast medium reaches a region of interest (ROI) of the object under medical examination;
    second memory means for temporarily storing a plurality of images, as contrast images, which have been acquired during a plurality of cardiac cycles, succeeding said one cardiac cycle, after the X-ray contrast medium has reached the ROI of the object;
    means for performing digital subtraction in synchronism with a cardiac phase of said object, between said successive mask images, read out from the first memory means, and said corresponding contrast images, read out from the second memory means; and
    means for controlling said digital subtraction means in such a manner that when the number of contrast images acquired within an arbitrary single cardiac cycle defined by two successive cardiac phases is smaller than that of the mask images stored in the first memory means and acquired within said single cardiac cycle, said subtraction means performs digital subtraction between all of said contrast images and the corresponding mask images, withholding a predetermined number of said mask images which do not correspond to said contrast images, with respect to the cardiac cycles, whereas, when the number of contrast images acquired within said single cardiac cycle is greater than that of the mask images acquired within said single cardiac cycle; said digital subtraction is carried out by utilizing all of said contrast images and by repeatedly utilizing at least one of said mask images, in addition to all of the corresponding mask images, with respect to the cardiac cycles.

2. An apparatus as claimed in claim 1, wherein said controlling means includes means for repeatedly using the last mask image acquired within said single cardiac cycle when multiple digital subtraction is performed in the subtraction means under the control of the subtraction control means.

3. An apparatus as claimed in claim 1, wherein said controlling means includes means for performing said digital subtraction in synchronism with at least an R-wave of the respective cardiac cycles.

4. An apparatus as claimed in claim 1, wherein said controlling means includes means for performing said digital subtraction in synchronism with at least R-waves and a T-wave of the respective cardiac cycles.

5. An apparatus as claimed in claim 1, further comprising:
    monitor means for displaying subtraction images obtained by said digital subtraction means.

6. An apparatus as claimed in claim 1, further comprising:
    electrocardiographic means connected to said subtraction control means for measuring said cardiac beats of the object.

7. An apparatus as claimed in claim 1, wherein said means for providing X-ray images includes means for acquiring said mask and contrast images at 30 frames per second.

8. A method of performing digital subtraction in an imaging apparatus, comprising the steps of:
    injecting an object with an x-ray contrast medium;
    acquiring a plurality of mask images during at least one cardiac cycle defined by successive cardiac phases before said X-ray contrast medium reaches a region of interest (ROI) of said object under medical examination;
    acquiring a plurality of contrast images during a plurality of cardiac cycles succeeding said one cardiac cycle after the X-ray contrast medium has reached the ROI of the object;
    storing said plurality of mask images acquired during said one cardiac cycle;
    storing said plurality of contrast images acquired during cardiac cycles succeeding said one cardiac cycle;
    reading out said stored mask and contrast images successively;
    subtracting digitally in synchronism with a cardiac phase of the object all of said plurality of contrast images from all of said plurality of mask images at times when the number of said contrast images is equal to the number of said mask images;
    subtracting digitally in synchronism with a cardiac phase of said object all of said plurality of contrast images from a corresponding number of said plurality of mask images at times when the number of said plurality of contrast images is less than the number of said plurality of mask images; and subtracting digitally in synchronism with a cardiac phase of said object a number of said plurality of contrast images from an equal number of said plurality of mask images, and subtracting digitally the acquired contrast images in excess of said number of said plurality of contrast images from at least one of said plurality of mask images at times when the number of said plurality of contrast images is greater than the number of said plurality of mask images.

9. A method according to claim 8, wherein the step of subtracting digitally at times when the number of said plurality of contrast images is greater than the number of said plurality of mask images comprises repeatedly subtracting digitally the acquired contrast images in excess of said number of said plurality of mask images from the last acquired mask image.

10. A method according to claim 8, wherein said steps of subtracting digitally are performed in synchronism with at least an R-wave of the respective cardiac cycles.

11. A method according to claim 8, wherein said steps of subtracting digitally are performed in synchronism with at least R-waves and a T-wave of the respective cardiac cycles.

12. A method according to claim 8, further comprising the step of displaying digital subtraction images obtained during the digital subtraction steps.

13. A method according to claim 8, wherein said steps of acquiring a plurality of mask and contrast images acquire said images at a rate of 30 frames per second.

* * * * *